(12) United States Patent
Oh et al.

(10) Patent No.: US 12,371,659 B2
(45) Date of Patent: Jul. 29, 2025

(54) MICROBEADS FOR CELL CULTURE AND METHOD OF MONITORING CELL CULTURE USING THE SAME

(71) Applicant: UNIVERSITY-INDUSTRY COOPERATION GROUP OF KYUNG HEE UNIVERSITY, Yongin-si (KR)

(72) Inventors: Tong In Oh, Hwaseong-si (KR); Sung Hyun Kim, Seoul (KR); Eun Ah Lee, Seoul (KR); Tae Woo Kim, Hwaseong-si (KR)

(73) Assignee: UNIVERSITY-INDUSTRY COOPERATION GROUP OF KYUNG HEE UNIVERSITY Korea, Yongin-si (KR)

( * ) Notice: Subject to any disclaimer, the term of this patent is extended or adjusted under 35 U.S.C. 154(b) by 231 days.

(21) Appl. No.: 18/306,152

(22) Filed: Apr. 24, 2023

(65) Prior Publication Data

US 2023/0257697 A1 Aug. 17, 2023

Related U.S. Application Data

(62) Division of application No. 16/091,673, filed as application No. PCT/KR2017/003753 on Apr. 6, 2017, now Pat. No. 11,667,888.

(30) Foreign Application Priority Data

Apr. 6, 2016 (KR) ........................ 10-2016-0042545
Apr. 6, 2017 (KR) ........................ 10-2017-0044494

(51) Int. Cl.
*C12N 5/00* (2006.01)
*G01N 33/50* (2006.01)

(52) U.S. Cl.
CPC ............ *C12N 5/0075* (2013.01); *C12N 5/00* (2013.01); *C12N 5/0068* (2013.01); *G01N 33/5005* (2013.01); *C12N 2531/00* (2013.01); *C12N 2533/30* (2013.01); *C12N 2533/40* (2013.01); *C12N 2537/00* (2013.01)

(58) Field of Classification Search
CPC .................................................. C12N 5/0075
See application file for complete search history.

(56) References Cited

U.S. PATENT DOCUMENTS

| 4,994,388 A | 2/1991 | Hillegas et al. |
| 5,256,616 A * | 10/1993 | Heller ............. C02F 1/32 |
| | | 428/407 |
| 5,707,859 A | 1/1998 | Miller et al. |
| 2013/0189723 A1 | 7/2013 | Felder et al. |

FOREIGN PATENT DOCUMENTS

| JP | 2005-185281 A | 7/2005 |
| KR | 10-0842378 B1 | 7/2008 |
| KR | 10-2009-0046857 A | 5/2009 |

OTHER PUBLICATIONS

Vrana et al., PLoSONE, May 2011, vol. 6, Issue 5, e20480, pp. 1-10 (Year: 2011).*
Wajgali et al., Biochemical Engineering Journal 70 (2013) 173-179 (Year: 2013).*
Communication dated Oct. 12, 2018, issued by the Korean Patent Office in counterpart Korean Patent Application No. 10-2017-0044494.
International Search Report for PCT/KR2017/003753 dated Jul. 10, 2017 [PCT/ISA/210].
MacKay et al., "Simulations of Interdigitated Electrode Interactions with Gold Nanoparticles for Impedance-Based Biosensing Applications", Sensors, vol. 15., pp. 22192-22208 (2015).
PLoSONE, May 2011, vol. 6, Issue 5, e20480, pp. 1-10 (Year: 2011).
Vidal et al., Acta Biomaterialia 9 (2013) 4935-4943 (Year: 2013).
Korean Office Action for Application No. 10-2017-0044494 dated Apr. 19, 2018.

* cited by examiner

*Primary Examiner* — Evelyn Y Pyla
(74) *Attorney, Agent, or Firm* — Sughrue Mion, PLLC

(57) ABSTRACT

Disclosed are microbeads for cell culture and a method of monitoring cell culture using the same. More particularly, each of the microbeads for cell culture according to an embodiment of the present invention include a core and a surface modification layer formed on a surface of the core. By using the method of monitoring cell culture with the microbeads for cell culture according to an embodiment of the present invention, cell culture may be carried out in highly scaled-up dimension and easily monitored.

5 Claims, 5 Drawing Sheets

MICROBEADS FOR CELL CULTURE AND METHOD OF MONITORING CELL CULTURE USING THE SAME

CROSS-REFERENCE TO RELATED APPLICATIONS

This application is a Rule 53(b) Divisional of U.S. application Ser. No. 16/091,673 filed Oct. 5, 2018, which is a National Stage of International Application No. PCT/KR2017/003753, filed on Apr. 6, 2017, which claims priority from Korean Patent Application No. 10-2016-0042545, filed on Apr. 6, 2016, and Korean Patent Application No. 10-2017-0044494, filed on Apr. 6, 2017. The contents of all of the above-identified applications are incorporated herein by reference in their entireties.

TECHNICAL FIELD

The present invention relates to microbeads for cell culture and a method of monitoring cell culture using the same.

BACKGROUND ART

Recently, biotechnology in the field of regenerative medicine, involving replacing or regenerating human tissues and organs using stem cells or progenitor cells such that the tissues and organs perform original functions thereof, is actively underway.

Most cells derived from solid tissues adhere to the surface of glass, plastic, or nylon as a single layer and proliferate thereon. To maximize stem cell yield, various bioreactors and incubators are being developed.

For effective stem cell yield, a surface area, to which the cells are attached, needs to be increased within limited volume increase using a biocompatible micro-bead, as a support for cell culture. Microbeads, providing a large surface area for cell proliferation, enable culturing adherent cells in suspension state and this method can effectively decrease culture volume.

However, when the cells are harvested upon confluence, the cells should be enzymatically detached from the microbead surface and separated from the plastic microbeads, which have small specific gravity difference from the cells. Accordingly, cells may be damaged, and cell loss may occur due to unclear separation between microbeads and cells.

In addition, to culture cells in safe and efficient way, materials of microbeads are limited to bio-compatible polymers. Therefore, microbeads are generally made of a natural or synthetic polymer having a specific gravity similar to cells.

As biodegradable or biocompatible materials clinically approved and currently used, there are a few polysaccharides, plastics such as polystyrene (PS), polyethylene (PE), polypropylene (PP), and synthetic polymers such as polylactic acid (PLA), poly-L-lactic acid (PLLA), poly (glycolic acid) (PGA), poly (lactic-co-glycolic acid) (PLGA), and poly-caprolactone (PCL).

The specific gravities of these substances are about 1.1 to 1.3, and the specific gravities of cell- or human-derived solid materials are also 1.2 or more. Because the specific gravities of the polymers are similar with those of cell- or human-derived solid materials, it is not easy to separate the polymers from the cell- or human-derived solid materials by centrifugation.

Meanwhile, when the cells are three-dimensionally cultured using microbeads made of glass or plastic, it is difficult to monitor the density of the cells. Accordingly, the cells might be cultured at high density for a longer period of time, unnoticed. In this case, intercellular cell-cell adhesion keeps increase along the culture period, making it difficult to completely separate the cells not only from microbeads but also from each other resulting in cell aggregates. Also, when the cells are separated from the microbeads using trypsin, it is difficult to monitor cells remaining on surfaces of the microbeads.

Although three-dimensional cell culture using microbeads has superior space efficiency and high expansion capacity, compared to two-dimensional culture, there are unignorable difficulties in monitoring cell proliferation state and harvesting process. Accordingly, there is a demand for cell culture technology to provide efficient cell expansion in limited culture volume and easy monitoring of cell growth for large-scale cell culture process.

RELATED ART DOCUMENT

Patent Document

Korean Patent No. 10-0842378 (Registered on Jun. 24, 2008, entitled "Specific gravity-increased supporter for cell culture and method of manufacturing the same")

DISCLOSURE

Technical Problem

One object of the present invention is to provide microbeads with low specific gravity for cell culture.

The other object of the present invention is to provide a method of culturing and monitoring cells on a large scale using the microbeads with low specific gravity.

Technical Solution

In accordance with one aspect of the present invention, provided is a microbead for cell culture, including a core; and a surface modification layer formed on a surface of the core.

The microbead for cell culture according to an embodiment of the present invention may further include a metal coating layer formed between the core and the surface modification layer.

The microbead for cell culture according to an embodiment of the present invention may have a specific gravity of 0.90 to 1.00.

The microbead for cell culture according to an embodiment of the present invention may have a spherical or disc shape.

In addition, the microbead for cell culture according to an embodiment of the present invention may have a diameter of 10 μm to 800 μm.

In the microbead for cell culture according to an embodiment of the present invention, the core may include at least any one selected from the group consisting of glass, silica, plastic such as polystyrene (PS), polyethylene (PE), polypropylene (PP), and biocompatible polymer such as poly lactic acid (PLA), poly L-lactic acid (PLLA), poly (glycolic acid) (PGA), poly (lactic-co-glycolic acid) (PLGA), and poly-caprolactone (PCL).

In the microbead for cell culture according to an embodiment of the present invention, the surface modification layer may include at least any one selected from the group consisting of gelatin, collagen, hyaluronic acid, chondroitin sulfate, alginate, chitosan, aminopropylsiloxane, poly-dopamine, poly-L-lysine, RGD peptide, and graphene.

In the microbead for cell culture according to an embodiment of the present invention, the metal coating layer may include at least any one selected from the group consisting of copper, silver, gold, titanium, and platinum.

The microbead for cell culture according to an embodiment of the present invention may be used to culture stem cells or progenitor cells.

In accordance with another aspect of the present invention, provided is a method of monitoring cell culture state using microbeads for cell culture, the method including a step of injecting the microbeads including a core and a surface modification layer formed on a surface of the core into a medium solution in a cell incubator for cell culture; a step of allowing cells to adhere onto surface modification layers of the microbeads and proliferate thereon; and a step of monitoring cell confluence based on the specific gravity change caused by the number of cells attached on the microbeads surface.

In the method of monitoring cell culture according to an embodiment of the present invention, the microbeads may further include a metal coating layer formed between the core and the surface modification layer.

In the step of the monitoring of the method of monitoring cell culture according to an embodiment of the present invention, floating positions of the microbeads in the medium solution may be monitored.

The positions of the microbeads may depend upon specific gravities of the microbeads.

In the method of monitoring cell culture according to an embodiment of the present invention, the cells attached to the surface modification layers of the microbeads may be stem cells or progenitor cells.

In the method of monitoring cell culture according to an embodiment of the present invention, the cells may include at least any one selected from the group consisting of bone marrow-derived mesenchymal stem cells (BM-MSC), adipose stem cells, cord blood stem cells, placental stem cells, epidermal cells, fibroblasts, dental pulp stem cells, periodontal ligament stem cells, stromal/progenitor cells isolated from any connective tissues, and chondrocytes.

Advantageous Effects

As apparent from the foregoing, a hydrophilic surface formed by surface modification of each of microbeads for cell culture according to an embodiment of the present invention, induces adsorption of a medium solution onto surfaces of the microbeads when the microbeads are immersed in the medium solution. Accordingly, cell may adhere to surfaces of the microbeads and proliferate thereon.

In addition, since the microbeads for cell culture according to an embodiment of the present invention have a lower specific gravity than a medium solution, the microbeads float in an upper layer (surface layer) of the medium solution at the beginning of cell culture. Subsequently, the specific gravities of the microbeads increase as cells adhere to surfaces of the microbeads and proliferate thereon, whereby an exhibited phenomenon that the microbeads sink in a lower part (lower layer) of the medium solution indicate the proliferation state of cells enabling intuitive monitoring.

In addition, by applying a cell culture method using the microbeads for cell culture according to an embodiment of the present invention, sinking degrees of the cell-seeded microbeads may be monitored. Accordingly, the rate of expansion culture may be predicted, and a population doubling time or an accumulative growth rate may be calculated by measuring sinking degrees of the microbeads.

In addition, with regard to the cell culture method using the microbeads for cell culture according to an embodiment of the present invention, microbead-cell complexes (microbeads including cells attached thereto and proliferating thereon) sunken in a lower part (lower layer) of a medium solution may be isolated and subcultured or subjected to cell analysis tests.

Further, with regard to the cell culture method using the microbeads for cell culture according to an embodiment of the present invention, the microbeads are treated with trypsin in a subculture process and then a degree of cell detachment may be intuitively determined by a floating degree of the microbeads. Accordingly, cell loss may be minimized.

BEST MODE

In the following description of the present invention, a detailed description of known functions and configurations incorporated herein will be omitted when it may make the subject matter of the present invention unclear. The terms used in the specification are defined in consideration of functions used in the present invention, and can be changed according to the intent or conventionally used methods of clients, operators, and users. Accordingly, definitions of the terms should be understood on the basis of the entire description of the present specification.

Hereinafter, the present invention is described in detail.

The present invention relates to microbeads for cell culture and a method of culturing cells using the same, more particularly to microbeads with low specific gravity for cell culture and a method of monitoring cell culture using the microbeads with low specific gravity.

Hereinafter, the microbeads for cell culture according to an embodiment of the present invention are described in detail with reference to FIGS. 1A and 1B.

Figure 1A:
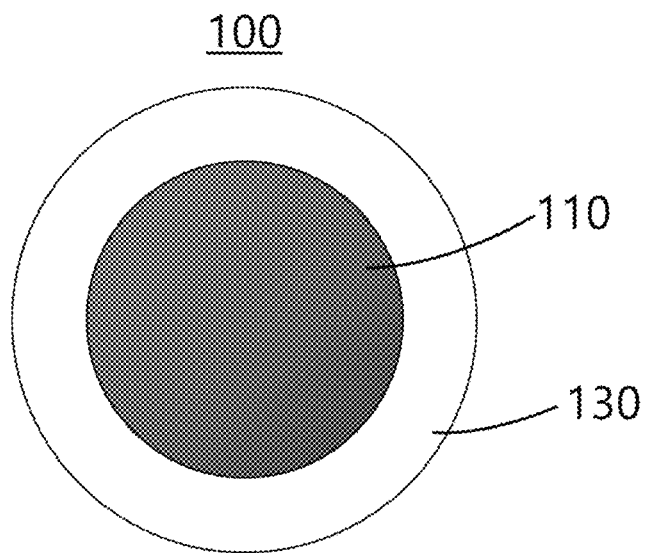
FIG. 1A is a sectional view schematically illustrating a microbead for cell culture according to an embodiment of the present invention.

FIG. 1A is a sectional view schematically illustrating a microbead for cell culture according to an embodiment of the present invention.

Referring to FIG. 1A, a microbead 100 for cell culture according to an embodiment of the present invention includes a core 110, and a surface modification layer 130 formed on a surface of the core 110.

With regard to the microbead 100 for cell culture according to an embodiment of the present invention, the core 110 is located at the center of the microbead 100 as illustrated in FIG. 1A.

The core 110 occupies the majority of the microbead 100. In particular, since the core 110 occupies the majority of the microbead 100, the core 110 may be an important factor determining the diameter, surface area, and the like of the microbead 100. For example, the diameter or surface area of the microbead 100 may increase with increasing size of the core 110. On the other hand, the diameter or surface area of the microbead 100 may be reduced with decreasing size of the core 110.

In addition, the core 110 may have a spherical or disc shape. The shape of the microbead 100 may be determined depending upon the shape of the core 110. For example, when the core 110 has a spherical shape, the surface modification layer 130 is uniformly formed on a surface of the core 110, whereby the microbead 100 including the core 110 and the surface modification layer 130 may have a spherical shape.

The diameter of the core 110 may be, for example, 10 μm to 800 μm, preferably 100 μm to 600 μm.

The shape of the core 110 may depend upon the diameter thereof. In particular, when the core 110 has a spherical shape, the core 110 may have almost the same diameter in all directions regardless of a maximum diameter and a minimum diameter. On the other hand, when the core 110 has a disc shape, the core 110 may have a maximum diameter and a minimum diameter, and various diameters in various directions thereof.

For example, the core 110 may be a spherical core having a diameter of 100 μm, or a disc-shaped core having a maximum diameter of 200 μm and a minimum diameter of 50 μm.

In addition, the core 110 may determine the specific gravity of the microbead 100. In particular, the specific gravity of the microbead 100 may be determined depending upon specific gravity of the core 110.

Specific gravity refers to a ratio of the mass of a substance to the mass of a reference substance with the same volume. Here, water at 1 atm and 4° C. is selected as a reference substance for solids and liquids, and the specific gravities of these solids and liquids corresponds to the densities thereof up to five decimal places. Accordingly, it may be considered that the specific gravities of the solids and liquids are the same as the densities thereof.

The core 110 may have a specific gravity of 0.800 to 1.000, preferably 0.900 to 0.999.

The core 110 may include a biocompatible inorganic compound or polymer.

The core 110 may be include, for example, an inorganic compound such as glass or silica, a plastic such as polystyrene (PS), polyethylene (PE), polypropylene (PP), and a biocompatible polymer such as, poly lactic acid (PLA), poly L-lactic acid (PLLA), poly (glycolic acid) (PGA), poly (lactic-co-glycolic acid) (PLGA), poly-caprolactone (PCL), or a mixture thereof.

With regard to the microbead 100 for cell culture according to an embodiment of the present invention, the surface modification layer 130 is formed on a surface of the core 110 as illustrated in FIG. 1A. In particular, the surface modification layer 130 is uniformly coated and formed on an entire surface of the core 110.

The surface modification layer 130 may be chemically hydrophilic, i.e., water-friendly. When the surface modification layer 130 is hydrophilic, a surface of the microbead 100 finally becomes hydrophilic.

When the microbead for cell culture 100 including the hydrophilic surface modification layer 130 is immersed in a medium solution according to an aspect of the present invention, a medium solution is adsorbed onto a surface of the microbead 100, and, due to the medium solution adsorbed onto the surface of the microbead 100, cells may well adhere to a surface of the microbead 100 and may proliferate thereon.

The surface modification layer 130 may have a thickness of, for example, 1 nm to 20 nm, preferably 1 nm to 10 nm.

The surface modification layer 130 may include, for example, at least any one selected from the group consisting of gelatin, collagen, hyaluronic acid, chondroitin sulfate, alginate, chitosan, poly-L-lysine, aminopropylsiloxane, poly-dopamine, RGD peptide, grapheme, and silane derivatives.

In addition, the surface modification layer 130 may exhibit cell survival increase effect due to an extracellular matrix component. Furthermore, cells may be uniformly dispersed on a surface of the microbead 100 by introducing a matrix component for promoting cell migration to the surface modification layer 130. Accordingly, cells can evenly distributed through the surface of microcarriers and the surface efficiency of the microbead 100 may be improved.

The microbead 100 for cell culture according to an embodiment of the present invention may have a core-shell structure wherein the core 110 is formed at the center of the microbead 100 and the surface modification layer 130 is formed on a surface of the core 110. More particularly, the core 110 is formed at the center of the microbead 100 to constitute a core structure, and the surface modification layer 130 is formed on a surface of the core 110 to constitute a shell structure.

The microbead 100 for cell culture according to an embodiment of the present invention is characterized by having low specific gravity. In particular, the microbead 100 for cell culture has a lower specific gravity than a medium solution for cell culture.

The microbead 100 for cell culture according to an embodiment of the present invention may have a specific gravity of 0.90 to 1.00, preferably 0.92 to 0.99, more preferably 0.95 to 0.99. The microbead 100 for cell culture according to an embodiment of the present invention has a specific gravity of 1.00 or less less than a medium solution generally having a specific gravity of 1.20.

The microbead 100 for cell culture according to an embodiment of the present invention has a spherical or disc shape. The shape of the microbead 100 may be affected by the shape of the core 110. For example, when the core 110 has a spherical shape, the surface modification layer 130 is uniformly formed on a surface of the core 110, whereby the microbead 100 including the core 110 and the surface modification layer 130 may have a spherical shape.

The microbead 100 for cell culture according to an embodiment of the present invention may have a diameter of 50 μm to 800 μm, preferably 100 μm to 600 μm, more preferably 200 μm to 500 μm. When the diameter of the microbead 100 for cell culture is 400 μm or more, cells may be easily separated from the microbead 100 upon separation of the cells, but a cell expansion rate may be low due to low surface to weight ratio. On the other hand, when the diameter of the microbead 100 is 10 μm or less, separation of cells from the microbead 100 may be difficult.

The diameter of the microbead 100 for cell culture may be varied depending upon the shape thereof. In particular, when the microbead 100 has a spherical shape, the microbead 100 may have almost the same diameter regardless of a maximum diameter and a minimum diameter, i.e., regardless of direction. On the other hand, when the microbead 100 has a disc shape, the microbead 100 may have a maximum diameter and a minimum diameter, and various diameters in various directions thereof.

For example, the microbead 100 may be a spherical core having of a diameter 150 μm, or a disc-shaped core having a maximum diameter of 200 μm and a minimum diameter of 100 μm.

Since the microbead 100 has a spherical or disc shape as described above, diameters in various directions of the microbead 100 may be similar when the microbead 100 has a shape similar to a spherical shape, and a minimum diameter and maximum diameter of the microbead 100 may be different from each other within the aforementioned range when the microbead 100 has a shape similar to a disc shape.

In addition, a surface of the microbead 100 for cell culture according to an embodiment of the present invention has a sufficiently flat shape that cells are easily attached (settled) thereto during cell culture.

Since the microbead 100 for cell culture according to an aspect of the present invention includes the hydrophilic surface modification layer 130, a medium solution is adsorbed onto a surface of the microbead 100 when the microbead 100 for cell culture is immersed in the medium solution. Since the medium solution adsorbed onto the surface of the microbead 100, cells may efficiently adhere to the surface of the microbead 100 and may proliferate thereon.

Meanwhile, the microbead 100 for cell culture according to an embodiment of the present invention may be a microbead for culturing stem cells or progenitor cells.

Stem cells refer to as cells capable of differentiating into various tissues that constitute the human body. Stem cells for restoring tissues and organs damaged and defective due to accident or disease are classified into embryonic stem cells and adult stem cells.

Embryonic stem cells have a risk of developing tumors and are difficult to use for therapeutic purposes due to ethical and legal problems. However, adult stem cells, which are obtained by culturing stem cells extracted from adipose tissue or bone marrow, are free from ethical and legal problems. Accordingly, issues with embryonic stem cells may be resolved.

Precursor cells refers to contracted stem cells. When specific differentiation direction of cells (X) corresponding to progeny has been determined, undifferentiated cells in a step prior to the differentiation of the cells (X) are called precursor cells. For example, neuroblasts correspond to precursor cells of nerve cells (neurons).

As examples of the stem cells or progenitor cells, there are adhesive cells such as adipocytes, fibroblasts, adult stem cells, preadipocytes, cord blood stem cells, placental stem cells, bone marrow-derived mesodermal stem cells (BM-MSC), epidermal cells, dental pulp stem cells, periodontal ligament stem cells, stromal/progenitor cells isolated from any connective tissues, or chondrocytes. In addition, a variety of established cell lines such uterine cancer cells (HeLa) may be used, and any cells capable of adhering to the microbeads 100 may be used without specific limitation.

To manufacture the microbead 100 for cell culture according to an embodiment of the present invention, for example, poly L-lactic acid (PLLA), as a biocompatible polymer constituting the core 110, is mixed and coated with gelatin. Accordingly, the microbead 100 for cell culture including the surface modification layer 130 formed of gelatin may be manufactured.

The polymeric microcore may be manufactured using microemulsion polymerization, dispersion polymerization, or the like. Meanwhile, an inorganic microcore may be prepared by the Stöber process or the like.

Meanwhile, to guarantee cell culture safety and minimize risks due to the characteristics of a microbead manufacturing technique and unpredictable variables in manufacturing the microbeads for cell culture according to the present invention, a biocompatible material is basically used and biologically safe material is preferred.

Hereinafter, a microbead for cell culture according to an embodiment of the present invention is described with reference to FIG. 1B.

Figure 1B:
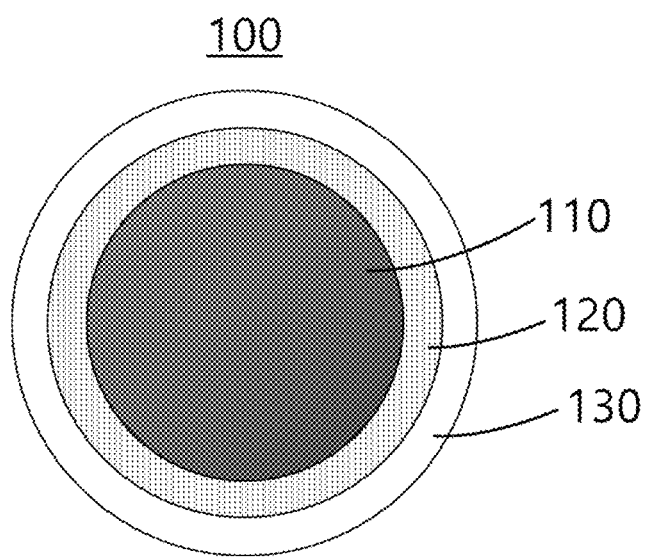
FIG. 1B is a sectional view schematically illustrating a microbead for cell culture according to an embodiment of the present invention.

FIG. 1B is a sectional view schematically illustrating a microbead for cell culture according to an embodiment of the present invention.

Referring to FIG. 1B, a microbead 100 for cell culture according to an embodiment of the present invention further includes a metal coating layer 120 formed between a core 110 and a surface modification layer 130.

In particular, the microbead 100 for cell culture according to the embodiment of the present invention includes the core 110, the metal coating layer 120 formed on a surface of the core 110, and the surface modification layer 130 formed on a surface of the metal coating layer 120.

Since the core 110 and the surface modification layer 130 are the same as those of the microbead 100 for cell culture which have been described with reference to FIG. 1A, description thereof is omitted.

With regard to the microbead 100 for cell culture according to the embodiment of the present invention, the core 110 is located at the center of the microbead 100 as illustrated in FIG. 1B.

The core 110 may have a spherical or disc shape. The shape of the microbead 100 may be determined depending upon the shape of the core 110. For example, when the core 110 has a spherical shape, the metal coating layer 120 and the surface modification layer 130 are uniformly formed on a surface of the core 110, whereby the microbead 100 including the core 110, the metal coating layer 120, and the surface modification layer 130 may have a spherical shape.

The diameter of the core 110 may be, for example, 10 μm to 800 μm, preferably 100 μm to 600 μm.

The core 110 may determine the specific gravity of the microbead 100. In particular, the specific gravity of the microbead 100 may be determined depending upon specific gravity of the core 110. The core 110 may have a specific gravity of 0.800 to 1.000, preferably 0.900 to 0.999.

The core 110 may include a biocompatible inorganic compound or polymer.

The core 110 may be include, for example, an inorganic compound such as glass or silica, a plastic such as polystyrene (PS), polyethylene (PE), polypropylene (PP), and a biocompatible polymer such as poly lactic acid (PLA), poly L-lactic acid (PLLA), poly (glycolic acid) (PGA), poly (lactic-co-glycolic acid) (PLGA), poly-caprolactone (PCL), or a mixture thereof.

With regard to the microbead 100 for cell culture according to an embodiment of the present invention, the metal coating layer 120 is formed on a surface of the core 110 as illustrated in FIG. 1B. In particular, the metal coating layer 120 is uniformly coated and formed on an entire surface of the core 110.

The metal coating layer 120 has a thickness of, for example, 1 μm to 100 μm, preferably 10 μm to 60 μm.

The metal coating layer 120 may include, for example, any one selected from the group consisting of conductive metals such as copper, silver, gold, titanium, and platinum, but the present invention is not limited thereto.

The metal coating layer 120 may perform impedance contrasting and density modulation. In particular, since the metal coating layer 120 is composed of a conductive metal as described above, an adhesion degree of cells to a microbead surface may be investigated by impedance measurement, and a predetermined density may be provided.

In addition, since the metal coating layer 120 is formed between the core 110 and the surface modification layer 130, adhesion therebetween may be increased.

With regard to the microbead 100 for cell culture according to an embodiment of the present invention, the surface modification layer 130 is formed on a surface of the metal coating layer 120 as illustrated in FIG. 1B. In particular, the surface modification layer 130 is uniformly coated and formed on an entire surface of the metal coating layer 120 formed on the surface of the core 110.

Accordingly, the surface modification layer 130 is formed on a surface of the metal coating layer 120, thereby constituting a final surface of the microbead 100.

The surface modification layer 130 may be chemically hydrophilic. When the surface modification layer 130 is hydrophilic, a surface of the microbead 100 finally becomes hydrophilic.

When the microbead for cell culture 100 including the hydrophilic surface modification layer 130 is immersed in a medium solution according to an aspect of the present invention, a medium solution is adsorbed onto a surface of the microbead 100, and, due to the medium solution adsorbed onto the surface of the microbead 100, cells may adhere to a surface of the microbead 100 and may proliferate thereon.

The surface modification layer 130 may have a thickness of, for example, 1 nm to 20 nm, preferably 1 nm to 10 nm.

The surface modification layer 130 may include, for example, at least any one selected from the group consisting of gelatin, collagen, hyaluronic acid, chondroitin sulfate, alginate, chitosan, poly-L-lysine, aminopropylsiloxane, poly-dopamine, RGD peptide, grapheme, and silane derivatives.

In addition, the surface modification layer 130 may exhibit cell survival increase effect of an extracellular matrix component. Furthermore, cells may be uniformly dispersed on a surface of the microbead 100 by introducing a matrix component for promoting cell migration to the surface modification layer 130. Accordingly, surface efficiency of the microbead 100 may be improved.

The microbead 100 for cell culture according to an embodiment of the present invention may have a core-shell structure wherein the core 110 is formed at the center of the microbead 100 and the metal coating layer 120 and the surface modification layer 130 are sequentially formed on a surface of the core 110. More particularly, the core 110 is formed at the center of the microbead 100 to constitute a core structure, and the metal coating layer 120 and the surface modification layer 130 are formed on a surface of the core 110 to constitute a two-layered shell structure.

The microbead 100 for cell culture according to an embodiment of the present invention is characterized by having low specific gravity. In particular, the microbead 100 for cell culture has a lower specific gravity than a medium solution for cell culture.

The microbead 100 for cell culture according to an embodiment of the present invention may have a specific gravity of 0.90 to 1.00, preferably 0.92 to 0.99, more preferably 0.95 to 0.99. The microbead 100 for cell culture according to an embodiment of the present invention has a specific gravity of 1.00 or less less than a medium solution generally having a specific gravity of 1.20.

The microbead 100 for cell culture according to an embodiment of the present invention has a spherical or disc shape. The shape of the microbead 100 may be affected by the shape of the core 110. For example, when the core 110 has a spherical shape, the metal coating layer 120 and the surface modification layer 130 are uniformly formed on a surface of the core 110, whereby the microbead 100 including the core 110, the metal coating layer 120, and the surface modification layer 130 may have a spherical shape.

To manufacture the microbead 100 for cell culture according to an embodiment of the present invention, for example, poly L-lactic acid (PLLA), as a biocompatible polymer constituting the core 110, may be mixed with silver hexafluorophosphate as a silver precursor. Accordingly, a surface of the core 110 formed of poly L-lactic acid may be coated with a silver coating layer 120 in reducing condition Subsequently, the core 110, which is formed of poly L-lactic acid, coated with the silver coating layer 120 is mixed and coated with gelatin, thereby finally manufacturing the microbead 100 for cell culture on which the gelatin surface modification layer 130 is formed.

The polymeric microcore may be manufactured using microemulsion polymerization, dispersion polymerization, or the like. Meanwhile, an inorganic microcore may be prepared by the Stöber process or the like.

Meanwhile, to guarantee cell culture safety and minimize risks due to the characteristics of a microbead manufacturing technique and unpredictable variables in manufacturing the microbeads for cell culture according to the present invention, a biocompatible material is basically used and biologically safe material is preferred.

Hereinafter, a method of monitoring cell culture using the microbeads for cell culture according to an embodiment of the present invention is described in detail referring to FIG. 2.

Figure 2:
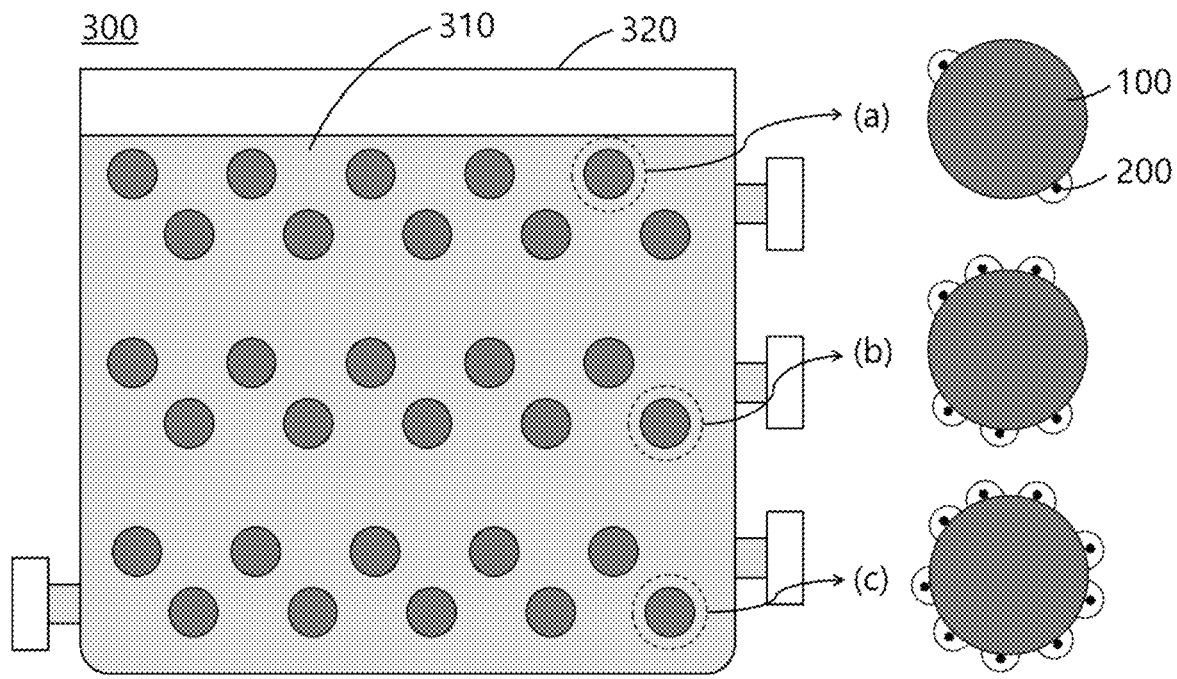
FIG. 2 is a view schematically illustrating cell culture monitoring using microbeads for cell culture according to an embodiment of the present invention.

FIG. 2 is a view schematically illustrating cell culture monitoring using microbeads for cell culture according to an embodiment of the present invention.

In the method of monitoring cell culture using the microbeads for cell culture according to an embodiment of the present invention, the microbeads 100 for cell culture according to an embodiment of the present invention are used.

In the method of monitoring cell culture according to an embodiment of the present invention, the microbead 100 has a lower specific gravity than a medium solution, and the specific gravity of the microbead 100 increases as cells adhere to a surface of the microbead 100 and proliferate thereon. In addition, the microbead 100 sinks downward in a medium solution as the specific gravity of the microbead 100 increases. Accordingly, the density of cells proliferated on a surface of the microbead 100 is monitored using a specific gravity difference in the microbead 100 dependent upon proliferation of cells thereon.

In the method of monitoring cell culture according to an embodiment of the present invention, a cell incubator 300 for cell culture includes a medium solution 310 and a cell culture chamber 320 containing the medium solution 310.

An impedance electrode (not shown) may be embedded in the cell incubator 300. By means of the impedance electrode, distribution of the microbeads 100 in the medium solution 310 may be numerically investigated.

The method of monitoring cell culture according to an embodiment of the present invention includes a step of injecting the microbeads 100 for cell culture, each of which includes the core 110, the metal coating layer 120 formed on a surface of the core 110, and the surface modification layer 130 formed on the metal coating layer 120, into the medium solution 310 in the cell incubator 300; a step of allowing the cells 200 to adhere to the surface modification layer 130 of the microbead 100 and proliferate thereon; and a step of monitoring the cell culture.

In particular, the medium solution 310 for cell culture is contained in the cell culture chamber 320 of the cell incubator 300, and the microbeads 100 for cell culture are injected into the medium solution 310.

Here, since the microbeads 100 for cell culture have a lower specific gravity than the medium solution 310, the microbeads 100 are present in a surface layer of the medium solution 310 when the microbeads 100 are injected into the medium solution 310. That is, the microbeads 100 float on an upper part (surface layer) of the medium solution 310 at the beginning of cell culture.

In the step of monitoring cell culture of the method of monitoring cell culture according to an embodiment of the present invention, the positions of the microbeads in the medium solution are monitored. Here, the positions of the microbeads depend upon specific gravities of the microbeads.

Referring to (a) of FIG. 2, the cells 200 begin to adhere to a surface of the microbead 100 with low specific gravity present in a surface layer of the medium solution 310 at the beginning of cell culture.

As illustrated in (a) of FIG. 2, the specific gravities of the microbeads 100 with low specific gravity present in a surface layer of the medium solution 310 gradually increase as the number of the cells 200 adhering to the microbeads 100 (hereinafter referred to as "microbead-cell complexes") increases, whereby the microbeads 100 gradually sink in the medium solution 310.

Referring to (b) of FIG. 2, the microbead-cell complexes, the specific gravities of which have increased due to proliferation of cells thereon, are exemplified as being present around a middle layer of the medium solution 310.

In particular, when about 60% of surfaces of the microbeads 100 are covered with the cells 200, the specific gravities of the microbead-cell complexes become similar to that of the medium solution 310. Accordingly, the microbead-cell complexes are present around a middle layer of the medium solution 310 as illustrated in (b) of FIG. 2.

As illustrated in (b) of FIG. 2, the specific gravities of the microbead-cell complexes further increase as the number of the cells 200 adhering to surfaces of the microbeads 100 present in the middle layer of the medium solution 310 increases.

Referring to (c) of FIG. 2, it can be observed that the microbead-cell complexes, the specific gravities of which have been further increased due to proliferation of the cells 200, sink close in a lower layer (bottom) of the medium solution 310.

In particular, when the number of the cells 200 covering about 60% of a surface of the microbead 100 increases and thus the cells 200 cover about 85% or more of a surface of the microbead 100, the microbead-cell complexes have a higher specific gravity than the medium solution 310. Accordingly, the microbead-cell complexes sink into a lower layer of the medium solution 310 as illustrated in (c) of FIG. 2.

That is, the step of monitoring cell culture using the microbeads 100 of the method of monitoring cell culture according to an embodiment of the present invention may include monitoring position change in the microbeads 100 due to adhesion of the cells 200 to the surface modification layers 130 of the microbeads 100 and thus sinkage of the microbead-cell complexes in a lower layer of the medium solution 310.

In particular, when the cells 200 adhere to surfaces of the microbeads 100 with low specific gravity, which have been present in a surface layer of the medium solution 310 due to having lower specific gravity than the medium solution 310, and proliferate thereon, the specific gravities of the microbead-cell complexes (the microbeads 100 to which the cells 200 are attached) increase. Accordingly, the microbead-cell complexes sink into a lower layer of the medium solution 310.

In other words, the microbead-cell complexes sink into a lower layer of the medium solution 310 due to increase in specific gravity thereof according to cell proliferation. Using such a phenomenon, a culture degree of the cells 200 adhering to surfaces of the microbeads 100 may be monitored.

Accordingly, the phenomenon that the microbead-cell complexes sink in the medium solution 310 as the cells 200 adhere to surfaces of the microbeads 100 and proliferate thereon may be observed with the naked eye or an impedance monitoring device. Therefore, cells may be mass-cultured and a proliferation state of these cells may be intuitively and easily monitored.

In addition, when cells are cultured using the microbeads 100 for cell culture according to an embodiment of the present invention, a proliferation state of the cells may be monitored. Accordingly, the rate of expansion culture may be predicted.

In addition, since the specific gravities of the microbead-cell complexes are changed depending upon the number of cells adhered to the surfaces of the microbeads 100 and proliferating thereon, the amount of microbeads 100 in each layer of a culture vessel may be determined by monitoring the sinking degree and amount of microbeads 100 in a medium solution by means of an impedance monitoring device. Accordingly, a population doubling time or an accumulative growth rate may be calculated.

In addition, the microbead-cell complexes (the microbeads 100 to which cells adhere and on which cells proliferate) sunken into a lower part (lower layer) of a medium solution may be separated using a method of culturing and monitoring cells using the microbeads for cell culture according to an embodiment of the present invention, and may be subcultured or subjected to cell analysis.

In addition, with regard to a method of monitoring subculture of cells using the microbeads for cell culture according to an embodiment of the present invention, the microbeads 100, the specific gravities of which have been increased due to cells attached thereto and thus which have sunken into a lower layer of a culture vessel, are separated from the cells by trypsin treatment in a subculture process, whereby the specific gravities thereof are decreased. Accordingly, the microbeads 100 float in a culture medium during the subculture. Since a cell collection degree may be determined by a floating degree of the microbeads 100, loss of cells may be minimized.

The method of monitoring cell culture using the microbeads for cell culture according to an embodiment of the present invention may be applied, without specific limitation, to adhesive cells, such as adhesive stem cells or progenitor cells, which may adhere to the surface modification layer 130 of the microbead 100.

As examples of adhesive cells applicable to the method of monitoring cell culture according to an embodiment of the present invention, there are bone marrow-derived mesodermal stem cells (BM-MSC), adipose stem cells, cord blood stem cells, placental stem cells, epidermal cells, fibroblasts, dental pulp stem cells, periodontal ligament stem cells, stromal/progenitor cells isolated from any connective tissues, chondrocytes, and the like. Hereinafter, the present invention will be described in more detail with reference to the following Examples. It should be understood that the examples are provided merely to concretely explain the spirit of the invention and therefore, there is no intent to limit the invention to the examples.

Example 1: Manufacturing of Microbeads for Cell Culture (Diameter: 500 µm)

A surface of polyethylene (0.91 to 0.96 g/cm$^3$), as a plastic material having relatively low density compared to water, is hydrophobic. Accordingly, polyethylene was hydrophilically surface-modified such that it was dispersed in an aqueous solution environment in which cells proliferated (note: the density of polypropylene is 0.855 to 0.946 g/cm$^3$)

A polyethylene cores (beads) used for experimentation included Rhodamine B, as a fluorescent molecule, and had a density of 0.99 g/ml or 0.995 g/ml. Here, the diameter of the polyethylene core was about 425 µm.

To etch surfaces of the polyethylene cores, a solution including distilled water, 30% ammonia water, and 30% hydrogen peroxide mixed in a ratio of 5:1:1 was fed into a glass vial. The solution was shaken every 10 minutes in a water bath over a period of two hours while maintaining temperature at 70° C. such that the polyethylene cores were dispersed.

After the reaction, the surface of polyethylene have become hydrophilic and the microbead have sunken right beneath the surface of solution. The diameters of the spherical microbeads surface-modified were about 500 µm.

Figure 3:
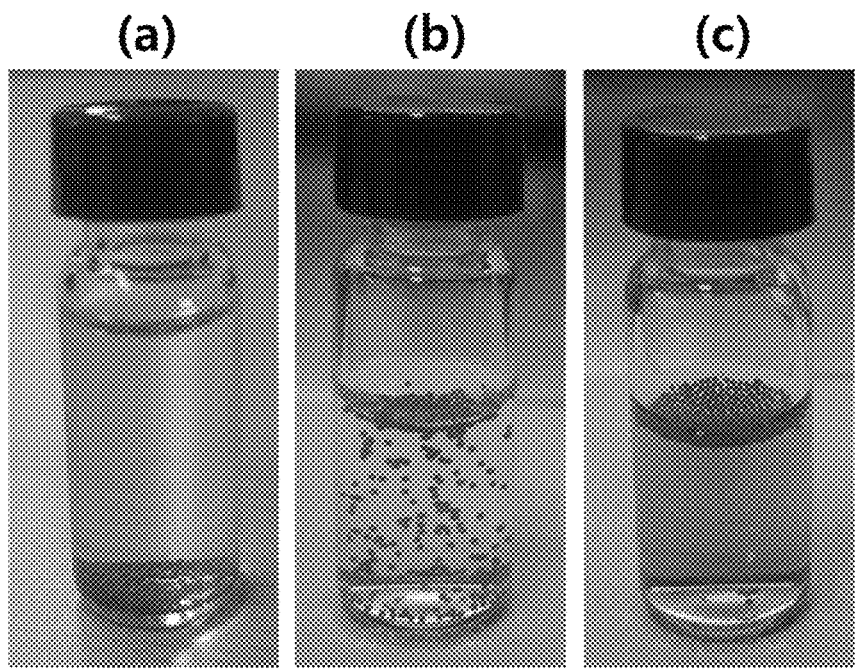
FIG. 3 is a view illustrating behavior of microbeads under various solution conditions according to an example (Example 1) of the present invention.

FIG. 3 is a view illustrating behavior of microbeads under various solution conditions according to an example of the present invention.

Referring to (a) to (c) of FIG. 3, the spherical microbeads surface-modified with trimethoxyaminopropylsilane in Example 1 tended to sink in (a) absolute ethanol (0.789 g/ml) having very low density, exhibited various sinking degrees when dispersed in (b) distilled water (1 g/ml), and tended to float near a culture medium surface in (c) a culture medium (1.04 g/ml) having a relatively high density.

Example 2: Manufacturing of Microbeads for Cell Culture (Diameter: 200 µm)

Spherical microbeads surface-modified with methoxy aminopropylsilane were manufactured in the same manner as in Example 1, except that polyethylene cores having a diameter of about 180 µm were used to prepare microbeads having a diameter of about 200 µm.

Example 3: Cell Culture Using Microbeads with Low Specific Gravity (Diameter: 500 µm) of Example 1 (for Two Hours)

340 surface-modified microbeads with a diameter of 500 µm of Example 1 and 3.5×10$^2$ mesodermal stem cells were mixed in a plastic tube. Temperature was maintained at 37° C. such that the cells were bound to the surfaces of the microbeads. Cell culture was performed for two hours while shaking every 10 minutes over a period of two hours such that the microbeads and the cells were dispersed.

Figure 4:
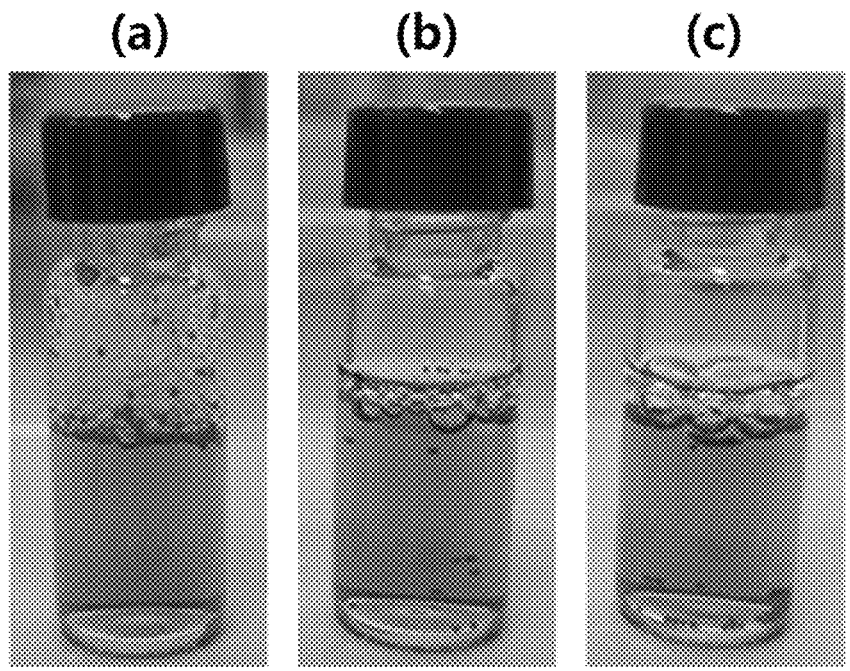
FIG. 4 is a view illustrating culture period-dependent behavior of microbeads in a culture medium according to an example (Example 3) of the present invention.

FIG. 4 is a view illustrating culture period-dependent behavior of microbeads in a culture medium according to an example of the present invention.

Referring to (a) to (c) of FIG. 4, as a result of the cell culture according to Example 3, the number of sunken microbeads tended to increase as cell culture time increased (from (a) to (c)).

Example 4: Cell Culture Using Microbeads with Low Specific Gravity (Diameter: 500 µm) of Example 1 (for Five Days)

Cell culture was carried out using the microbeads in the same manner as in Example 3, except that a cell culture time was extended to five days.

Figure 5:
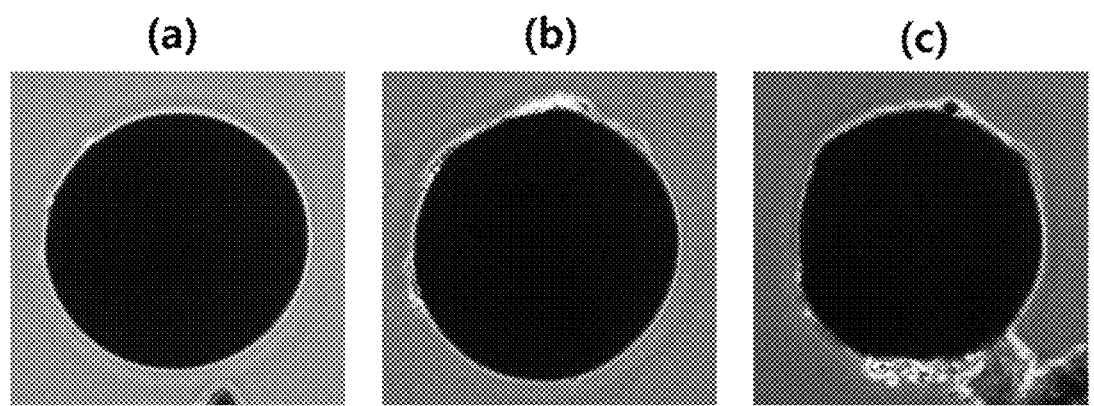
FIG. 5 is a view illustrating an adhesion degree of cells to microbeads depending upon position thereof in a culture medium according to an example (Example 4) of the present invention.

FIG. 5 is a view illustrating an adhesion degree of cells to microbeads depending upon position thereof in a culture medium according to an example of the present invention.

Referring to (a) to (c) of FIG. 5, after culturing cells in a plastic tube for five days according to Example 4, microbeads distributed in (a) an upper layer (a surface layer), (b) an middle layer, and (c) a lower layer (bottom layer) of a culture medium were fractionized and adhesion degrees of cells on surfaces of the microbeads were observed by means of an inverted microscope. As a result, it was confirmed that the number of cells attached to each of the microbeads increased in proportion to sinking degrees of the microbeads.

Figure 6:
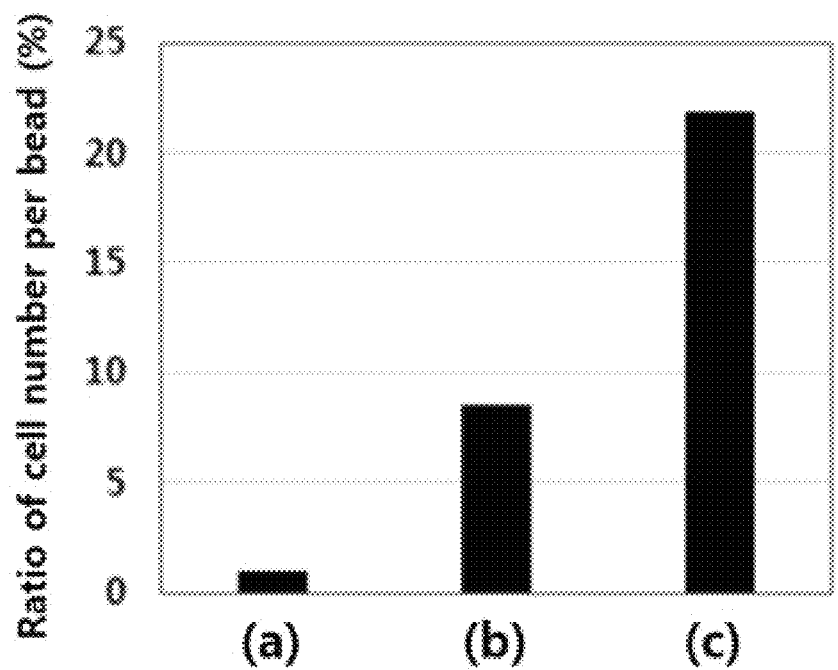
FIG. 6 illustrates an MTT assay (as a cytotoxicity and cell survival rate test method) result showing a correlation between a growth degree of cells adhered to microbeads and a sedimentation degree of the microbeads according to an example (Example 4) of the present invention.

FIG. 6 illustrates an MTT assay (as a cytotoxicity and cell survival rate test method) result showing a correlation between a growth degree of cells adhered to microbeads and a sedimentation degree of the microbeads according to an example of the present invention.

Referring to (a) to (c) of FIG. 6, a growth rate of cells adhered to and proliferating on the microbeads according to Example 4 was investigated by MTT assay. As a result, it was confirmed that an average number of cells attached to each of the microbeads increased in proportion to sinking degrees of the microbeads (cell proliferation degree: (a) upper layer<(b) middle layer<(c) lower layer).

After the MTT assay, to compare absorbance values of the microbeads in the upper layer, the middle layer, and the lower layer, the absorbance of each of the upper layer, the middle layer, and the lower layer was divided by the number of the microbeads present in each thereof. As a result, the middle layer exhibited an absorbance of about 8.5 times and the lower layer exhibited an absorbance of about 21.9 times, compared to the upper layer. Such a result indicates that the number of cells attached to each of the microbeads increases in proportion to sinking degrees of the microbeads.

Example 5: Monitoring Cell Culture Using Microbeads with Low Specific Gravity (Diameter: 200 μm) of Example 2

50 mg of the surface-modified microbeads with a diameter of 200 μm (corresponding to $1.27 \times 10^4$ microbeads) of Example 2 were fed into each plastic tubes. To these plastic tubes, (a) $4 \times 10^2$ mesodermal stem cells and (b) $1.2 \times 10^6$ mesodermal stem cells respectively mixed with 1 ml of a serum-free culture medium were respectively added. Temperature was maintained at 37° C. such that the cells were bound onto the microbeads. Cell culture was performed for four hours while shaking every 10 minutes such that the microbeads and the cells were satisfactorily dispersed.

Here, (a) $4 \times 10^2$ cells inoculated with 50 mg of the microbeads with a diameter of 200 μm was capable of covering 1/1,000 of an entire surface area of microbeads in each plastic tube, and (b) $1.2 \times 10^6$ cells inoculated with 50 mg of the microbeads with a diameter of 200 μm was enough to cover an entire surface area of microbeads in each plastic tube.

After four hours, 4 ml of a culture medium containing 20% of serum was added to each of the tubes, and cell culture was further performed for 24 hours.

Figure 7:
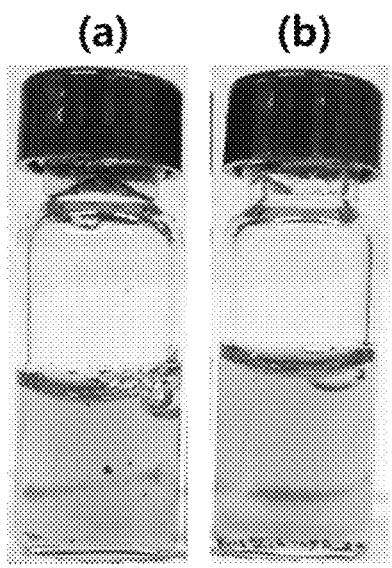
FIG. 7 illustrates behavior of microbeads in a culture medium dependent upon the number of cells initially inoculated with the microbeads according to an example (Example 5) of the present invention.

FIG. 7 illustrates behavior of microbeads in a culture medium dependent upon the number of cells initially inoculated with microbeads according to an example of the present invention.

Referring to (a) and (b) of FIG. 7, as a result of the cell culture according to Example 5, the number of sunken microbeads tended to increase as the number of cells injected to the microbeads increased ((a) $4 \times 10^2$ < (b) $1.2 \times 10^6$).

Figure 8:
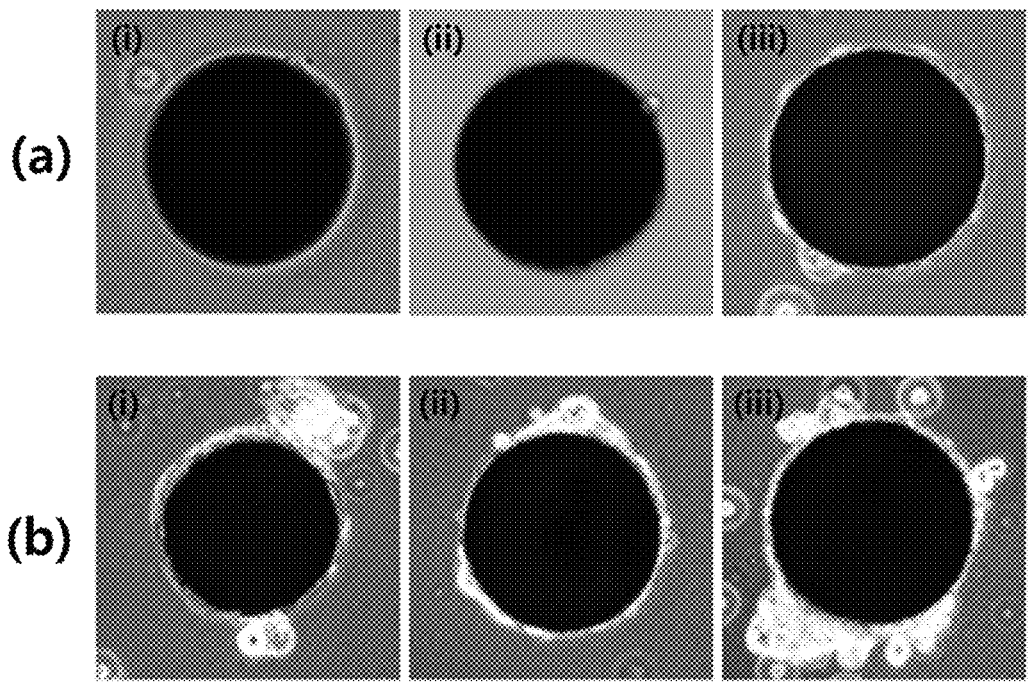
FIG. 8 illustrates an adhesion degree of cells to microbeads depending upon position thereof in a culture medium according to an example (Example 5) of the present invention.

FIG. 8 illustrates an adhesion degree of cells to microbeads depending upon position thereof in a culture medium according to an example of the present invention.

Here, (i), (ii), and (iii) are representative picture of microbead took from each of the groups (a) and (b) obtained after observing the groups (a) and (b) several times.

Referring to (a) and (b) of FIG. 8, (a) the microbeads bound with $4 \times 10^2$ cells and (b) the microbeads bound with $1.2 \times 10^6$ were obtained according to Example 5, and adhesion degrees of cells on surfaces thereof were observed by means of an inverted microscope. As a result, it was confirmed that sinking degrees of the microbeads increased in proportion to the number of cells adhered to each of the microbeads ((a)<(b)).

Figure 9:
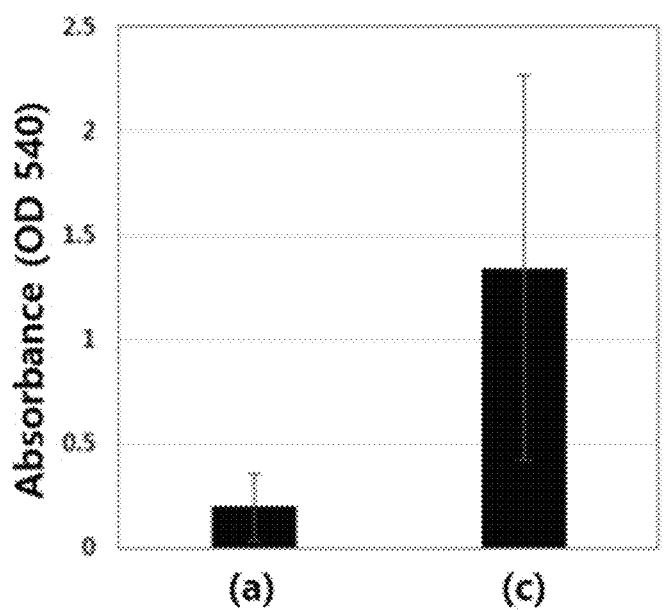
FIG. 9 illustrates an adhesion degree of cells to microbeads investigated by MTT assay (as a cytotoxicity and cell survival rate test method) according to an example (Example 5) of the present invention.

FIG. 9 illustrates an adhesion degree of cells to microbeads investigated by MTT assay (as a cytotoxicity and cell survival rate test method) according to an example of the present invention.

Here, OD 540 on the y axis is an abbreviation for Optical Density 540 and represents the absorbance after MTT assay Referring to (a) and (c) of FIG. 9, survival rates of cells adhered to the microbeads were compared by MTT assay according to Example 5. As a result, it was confirmed that an adhesion degree of cells on each of the microbeads increased in proportion to a sinking degree of the microbeads (cell adhesion degree: (a) upper layer<(c) lower layer).

Although the present invention has been described through limited examples and figures, the present invention is not intended to be limited to the examples. Those skilled in the art will appreciate that various modifications, additions and substitutions are possible, without departing from the scope and spirit of the invention. Therefore, it should be understood that there is no intent to limit the disclosure to the embodiments disclosed, rather, the disclosure is to cover all modifications, equivalents, and alternatives falling within the spirit and scope of the disclosure as defined by the claims.

The invention claimed is:

1. A method of monitoring cell culture using microbeads for cell culture, the method comprising:
   a step of injecting the microbeads for cell culture comprising a core, a metal coating layer formed on a surface of the core, and a surface modification layer formed on a surface of the metal coating layer into a medium solution including cells in a cell incubator;
   a step of allowing cells to adhere onto surface modification layers of the microbeads and proliferate thereon; and
   a step of monitoring the cell culture,
   wherein the metal coating layer is formed between the core and the surface modification layer,
   wherein the metal coating layer is an impedance analysis layer,
   wherein the microbead for cell culture is configured to monitor an adhesion degree of cells on the surface of the microbead and an amount of the micro-bead in a medium by location using impedance,
   wherein the surface modification layer has a thickness of 1 nm to 20 nm, and
   wherein the metal coating layer has a thickness of 1 μm to 100 μm.

2. The method according to claim 1, wherein, in the step of the monitoring, positions of the microbeads in the medium solution are monitored.

3. The method according to claim 2, wherein the positions of the microbeads depend upon specific gravities of the microbeads.

4. The method according to claim 1, wherein cells adhered to the surface modification layers of the microbeads are stem cells or progenitor cells.

5. The method according to claim 4, wherein the cells comprise at least any one selected from the group consisting of adult stem cells, preadipocytes, cord blood stem cells, placental stem cells, dental pulp stem cells, bone marrow-derived mesodermal stem cells (BM-MSC), periodontal stem cells and stromal/progenitor cells isolated from any connective tissues.

* * * * *